(12) United States Patent
Weckström et al.

(10) Patent No.: US 7,069,768 B2
(45) Date of Patent: Jul. 4, 2006

(54) METHOD AND APPARATUS FOR ELIMINATING AND COMPENSATING THERMAL TRANSIENTS IN GAS ANALYZER

(75) Inventors: Kurt Weckström, Esbo (FI); Heikki Haveri, Huhmari (FI); Mika Hietala, Espoo (FI)

(73) Assignee: Instrumentarium Corp., Helsinki (FI)

( * ) Notice: Subject to any disclaimer, the term of this patent is extended or adjusted under 35 U.S.C. 154(b) by 103 days.

(21) Appl. No.: 10/863,810

(22) Filed: Jun. 8, 2004

(65) Prior Publication Data

US 2005/0268690 A1    Dec. 8, 2005

(51) Int. Cl.
*G01N 25/00*    (2006.01)

(52) U.S. Cl. ..................................... 73/23.2; 73/25.01

(58) Field of Classification Search ................. 73/23.2, 73/25.01
See application file for complete search history.

(56) References Cited

U.S. PATENT DOCUMENTS

| | | | |
|---|---|---|---|
| 4,671,664 | A | 6/1987 | Fabinski et al. |
| 5,092,342 | A | 3/1992 | Hattendorff et al. |
| 5,542,285 | A | 8/1996 | Merilianen et al. |
| 6,694,800 | B1 | 2/2004 | Weckstrom et al. |
| 2003/0177814 | A1 | 9/2003 | Weckström et al. |
| 2003/0205673 | A1 | 11/2003 | Williams |

FOREIGN PATENT DOCUMENTS

EP    0 462 744    12/1991

OTHER PUBLICATIONS

European Search Report, Sep. 14, 2005.

*Primary Examiner*—Hezron Williams
*Assistant Examiner*—Rodney Frank
(74) *Attorney, Agent, or Firm*—Andrus, Sceales, Starke & Sawall, LLP

(57) ABSTRACT

The invention concerns a gas analyzer comprising: a measuring volume (2), a radiation source (1) for providing a beam to pass said measuring volume; a heat sink (16) for said radiation source; at least one thermal detector (3) having a hot junction within a support structure and receiving the radiation and a cold junction for reference within the same support structure and protected from said radiation; at least one optical bandpass filter (9) between said hot junction and said radiation source; and a thermal mass (11), which is formed of a material having high thermal conductance. The thermal mass has a cavity with a bottom step (34) and a rim (32), and a first length therebetween. The support structure has a frontal edge (35) and a base plate lip (33), and a second length therebetween. There is a radial gap between the thermal mass and the support structure. Press means urge said support structure in the cavity, whereupon a more efficient thermal contact is either between said frontal edge and said bottom step, or between said base plate lip and said rim. A first thermal barrier (17) is between the heat sink and the thermal mass, and a second thermal barrier (22) surrounds the thermal mass. A shield (19) formed of a material having high thermal conductance covers said second thermal barrier and is in thermal contact with said heat sink.

50 Claims, 5 Drawing Sheets

METHOD AND APPARATUS FOR ELIMINATING AND COMPENSATING THERMAL TRANSIENTS IN GAS ANALYZER

FIELD OF THE INVENTION

The invention relates a gas analyzer and a method for determining the concentration of at least one gas component present in a sample gas mixture. The arrangement comprises a radiation source for providing a beam of electromagnetic radiation; a heat sink for said radiation source; at least one thermal detector having an active radiation detecting sensor element in a support structure, and a reference sensor element within the same support structure and protected from said radiation, said thermal detector generating an output signal indicative of a property of said at least one gas component; and at least one optical bandpass filter between said active radiation detecting sensor element and said radiation source; as well as a thermal mass: formed of a material having high thermal conductance; having a cavity; being at least in partial thermal contact with said support structure inside said cavity; and extending towards the radiation source.

BACKGROUND OF THE INVENTION

A characteristic of a thermopile detector is that thermal gradients or transients in its external housing, noticeable especially in small analyzers with small thermal mass, will cause an offset error in the detector signal, which degrades measurement accuracy. The thermopile is a very sensitive detector containing a plurality of thermocouple junctions. In a typical analyzer it has been measured that the signal change corresponding to the absorption caused by 0,1% by volume of $CO_2$ in a sample gas is about 2 µV. The temperature difference in the thermopile detector would then be only about 0.13 mK. It is therefore easy to understand that even small temperature gradients in the thermopile housing may cause considerable measurement errors.

In general, thermal gradients can be divided into static state thermal gradients and dynamic state thermal gradients. Static state thermal gradients appear in constant conditions when the heat flow from the ambient into the analyzer is constant and the heat flow inside the analyzer is constant. Static state thermal gradient appears as temperature difference between any two points in the analyzer and when it appears over the thermopile detector it causes an offset error into the detector signal. If all the non-idealities of the thermopile detector can be ignored the offset error in the detector signal caused by the static state thermal gradient remains constant over the time as the system state remain constant. The dynamic state thermal gradient or transient is a gradient that changes in time as the ambient temperature changes or the internal temperature of the analyzer changes. When the ambient temperature or the internal temperature of the analyzer changes the thermal flow in the analyzer causes a variable temperature difference between any two points in the analyzer and when it appears over the thermopile detector it causes a variable offset error into the detector signal. Such errors occur with a change of the external housing temperature after, e.g., a cold start-up of the analyzer or due to a change in the ambient temperature. The amplitude of the error caused by the dynamic state thermal gradient is proportional to the temperature difference over the thermopile detector, which in turn is proportional to the rate of temperature change. The amplitude of the error decreases as the rate of temperature change decreases and as the dynamic state thermal gradient approaches the static state thermal gradient the error caused by dynamic state thermal gradient finally becomes zero and the error caused by the static state thermal gradient remains.

The U.S. Pat. No. 6,694,800 a gas analyzer is described where a beam of collimated electromagnetic radiation is provided by a fixed source, and is directed to pass said measuring volume to meet thermopile detector(s) generating an output signal indicative of a property of said at least one gas component of said mixture in the measuring volume. The thermal offset and the drift are eliminated in this analyzer by minimizing the thermal gradients over the complete detector housing, including its electrical connections. Electrical wires are composed of materials and have dimensions producing an overall thermal conductance substantially lower than that of said electrical pins. The electrical wires are connected with the electrical contact pins either directly or indirectly, and enclosed in the thermal mass together with said detector housing(s), and the electrical wires extend from the cavity through the thermal mass to the outside thereof with at least one exit point at said outer surface. Theoretically there should not be any signal offset in a thermopile without radiation reaching its sensitive area and in order to achieve this there should not be any temperature difference between the hot junctions in the sensitive area and the cold reference junctions of the thermopile. This further means that no thermal gradient can be allowed within the detector housing in spite of the relatively high heat flow and small thermal mass of the small sized analyzer. There will always be a gradient from the analyzer to the ambient but according to the invention this gradient is transferred away from the detector housing and its electrical connections by completely enclosing the detector housing in a material with good thermal conductivity.

The U.S. Pat. No. 6,694,800 thus introduces a solution for static state temperature compensation, which means that ambient temperature or internal temperature flows of the analyzer remain constant. As the detector output voltage is proportional to the temperature difference between the active and the reference junctions of the thermopile detector, it is easy to understand detectors sensitiveness to static temperature flows or static state temperature gradients. Therefore it is easy to understand also that variable temperature flows or temperature transients, in other words dynamic state temperature gradients should be eliminated also.

The U.S. Pat. No. 5,542,285 describes a method and apparatus for compensating transient errors in gas analyzer equipment caused by ambient temperature changes. A characteristic of the thermopile is that with a change of its external housing temperature after, e.g., a cold start-up of the analyzer or due to an ambient temperature change the detector output will contain a transient error which degrades measurement accuracy over the duration of the transient state. The invention is based on compensating the thermal drift of a gas analyzer by means of measuring the temperature of the thermal infrared detector, or the temperature of the detector package advantageously having the same temperature as the detector or, advantageously, the temperature of the analyzer body piece having the same temperature as the detector package, and then adding a correction signal dependent on the temperature rate of change to the detector output signal. A shortcoming of this compensation method is that the actual error source causing the temperature transient error at the detector output is not corrected, but the amplitude and the rate of change of thermal detectors or its conductive housings temperature is measured, which is thought to correspond the actual error signal, and a correction signal in certain sense proportional to measured temperature signal is finally added to the detector output signal as correction. Measuring the temperature in one or even few points of the detector case or its thermally conductive housing does not indicate the source or the direction of heat flow accurately enough to predict whether the temperature change is caused by ambient temperature change, internal thermal transient caused by e.g. a cold start-up of the analyzer or e.g. a fan cooling the one side of the sensor. Adding multiple temperature sensors in the gas analyzer body makes the analyzer uneconomical and functioning complicated through heavy computing.

SUMMARY OF THE INVENTION

It is an object of the present invention to overcome the shortcomings of the above described prior-art techniques and to achieve a novel type of non-dispersive gas analyzer for eliminating offset and drift caused by the ambient temperature transients. Especially it is an object of the present invention to eliminate the large offset signal and drift caused by the internal thermal transients flowing from the radiation source along the analyzer body towards thermal detector(s) during said analyzer start-up with a simple and cheap mechanical thermal flow design. It is also an object to equalize effects of thermal flows upon thermal detector between the internal temperature transient and ambient temperature transient to improve the functioning of known transient error compensation methods. Further it is an object of the present invention to achieve a cheap and a small sized or miniature gas analyzer in which also economic commercially available thermopile detectors may be used. Furthermore it is an object of the present invention to fulfill EMC (electromagnetic compatibility) requirements, which is a problem for electrically sensitive equipment used in demanding hospital environment.

The problems described above can be overcome and the objects defined above can be reached by the device according to the invention, and by the method according to the invention.

According to the first aspect of the invention it is provided a gas analyzer comprising: a measuring volume for through flow of a sample gas mixture, at least one gas component of which is to be analyzed for determining its concentration in said mixture, and having first and second transparent ends; a radiation source for providing a beam of electromagnetic radiation having a wavelength range, said beam directed to pass said measuring volume through said first and second transparent ends thereof; a heat sink for said radiation source; at least one thermal detector having an active radiation detecting sensor element within at least one support structure and receiving the radiation exiting said measuring volume, said thermal detector having a reference sensor element within the same support structure and protected from said radiation, said thermal detector generating an output signal indicative of a property of said at least one gas component of said mixture in the measuring volume; at least one optical bandpass filter between said active radiation detecting sensor element and said radiation source; a thermal mass: formed of a material having high thermal conductance; having a cavity; being at least in partial thermal contact with said support structure inside said cavity; and extending towards the radiation source; a first thermal barrier between the heat sink and the thermal mass; a second thermal barrier surrounding the thermal mass and extending towards the heat sink; and shield formed of a material or materials having high thermal conductance; said shield being at least in thermal contact with said heat sink, and covering said second thermal barrier.

According to the second aspect of the invention it is provided a gas analyzer comprising: a measuring volume for through flow of a sample gas mixture, at least one gas component of which is to be analyzed for determining its concentration in said mixture, and having first and second transparent ends; a radiation source for providing a beam of electromagnetic radiation having a wavelength range, said beam directed to pass said measuring volume through said first and second transparent ends thereof; a heat sink for said radiation source; at least one thermal detector having an active radiation detecting sensor element within at least one support structure and receiving the radiation exiting said measuring volume, said thermal detector having a reference sensor element within the same support structure and protected from said radiation, said thermal detector generating an output signal indicative of a property of said at least one gas component of said mixture in the measuring volume; at least one optical bandpass filter between said active radiation detecting sensor element and said radiation source; a thermal mass: formed of a material having high thermal conductance; having a cavity with a bottom step and a rim, and a first length therebetween; and extending towards the radiation source; in said at least one support structure: a frontal edge and a base plate lip, and a second length therebetween; a radial gap between the thermal mass and the housing; and press means urging said support structure in said cavity; whereupon, depending on the predetermined difference between said first length and said second length, a more efficient thermal contact is either between said frontal edge and said bottom step, or between said base plate lip and said rim.

According to the third aspect of the invention it is provided a method for determining a concentration of at least one gas component in a sample gas mixture by providing a radiation source that directs a beam of electromagnetic radiation having a wavelength range to pass a measuring volume, through which said sample gas mixture is delivered, and to pass at least one optical bandpass filter, and by detecting intensity of a rest radiation exiting said measuring volume and said at least one optical bandpass filter, the method comprising the steps of: transferring generated heat from said radiation source to a heat sink; allowing said rest radiation to hit an active radiation detecting sensor element in a thermal detector and protecting a reference sensor element of the same thermal detector from said rest radiation; said thermal detector having a support structure carrying said detecting and reference sensor elements, and generating an output signal indicative of a property of said at least one gas component of said mixture in the measuring volume; evening out temperature differences around said thermal detector by allowing heat to be conducted in a thermal mass having high thermal conductance and dimensions to surround said thermal detector and extending towards said radiation source; thermally isolating said thermal mass, said measuring volume, and said radiation source from ambience by at least one thermal barrier; conducting said generated heat from said heat sink along at least thermally conductive outer surface layers; arranging one or several contacts between said support structure of the thermal detector and said thermal mass such that mean heat flow times between said one or several contacts and said reference sensor element along a convection route and a conduction route are at least approaching each other.

The invention is based on minimizing the static state and the dynamic state thermal gradients over the thermal detector in the gas analyzer. This is attained by a gas analyzer in which said thermal detector(s) is enclosed in the thermally conductive mass comprising of said housing, housing enclosed in thermally conductive mass said thermal mass, thermal mass together said housing and said thermal detector(s) enclosed in thermally and electrically conductive layer said EMC-housing, the EMC-housing comprising said thermally and electrically conductive EMC-shield connected to thermally and electrically conductive said heat sink of radiation source, and thermally and electrically conductive electrical ground plane of said electronic circuit board, a thermal barrier between said housing and said EMC-housing, thermal barrier having a cavity for radiation to pass through the housing from said radiation source in to said thermal detector(s), the housing and the thermal barrier further having a cavity for the electrical wires, the electrical wires connected between detector(s) and the electronic circuit board, the electrical wires enclosed in the thermally conductive housing extending from the cavity through the housing and the cavity through the thermally insulating layer towards the electronic circuit board with at least one exit point, and the electrical wires composed of materials and have dimensions producing a low overall thermal conductance.

Furthermore the analyzer according to the invention is thermally designed in the way that internal temperature transients or ambient temperature changes have an equivalent thermal effect on the thermopile detector output signal that can be determined by measuring the detector temperature and the thermal effect on the thermopile detector output signal can further be compensated by adding a correction signal to the thermopile output signal. This is done by conducting internal temperature flows caused by the radiation source but also conducting temperature flows coming from the ambient into the EMC-housing made of material with good thermal conductivity, the EMC-housing distributing the thermal flow through its thermally conductive surfaces evenly around the completely enclosed thermal mass, the thermal detector in thermally conductive thermal mass receiving the thermal flow evenly from each direction through the thermal barrier between the EMC-housing and the thermal mass, the thermal barrier damping the thermal flow in to the thermal mass along its length in such proportion that the effect of internal temperature transients is equivalent to the effect of ambient temperature change over the thermal detector.

BRIEF DESCRIPTION OF THE DRAWINGS

The foregoing summary, and the following detailed description of the preferred embodiments of the present invention, will be better understood when read in conjunction with the accompanying drawings, in which:

FIGS. 5a–5c illustrates the first embodiment of the inventive gas analyzer seen in the longitudinal section of the analyzer parallel with the radiation beam, i.e. along the optical axis, and a detailed graph of five different thermal gradients at five different times from start-up of this inventive analyzer, and a graph of thermopile signal during the start-up of this inventive analyzer respectively. This embodiment respects to constructions of FIGS. 1 and 8a.

FIG. 8a is an enlarged view of area I in FIG. 1, and FIG. 8b is an enlarged view of area II in FIG. 2.

DETAILED DESCRIPTION OF THE PREFERRED EMBODIMENTS

Figure 1:
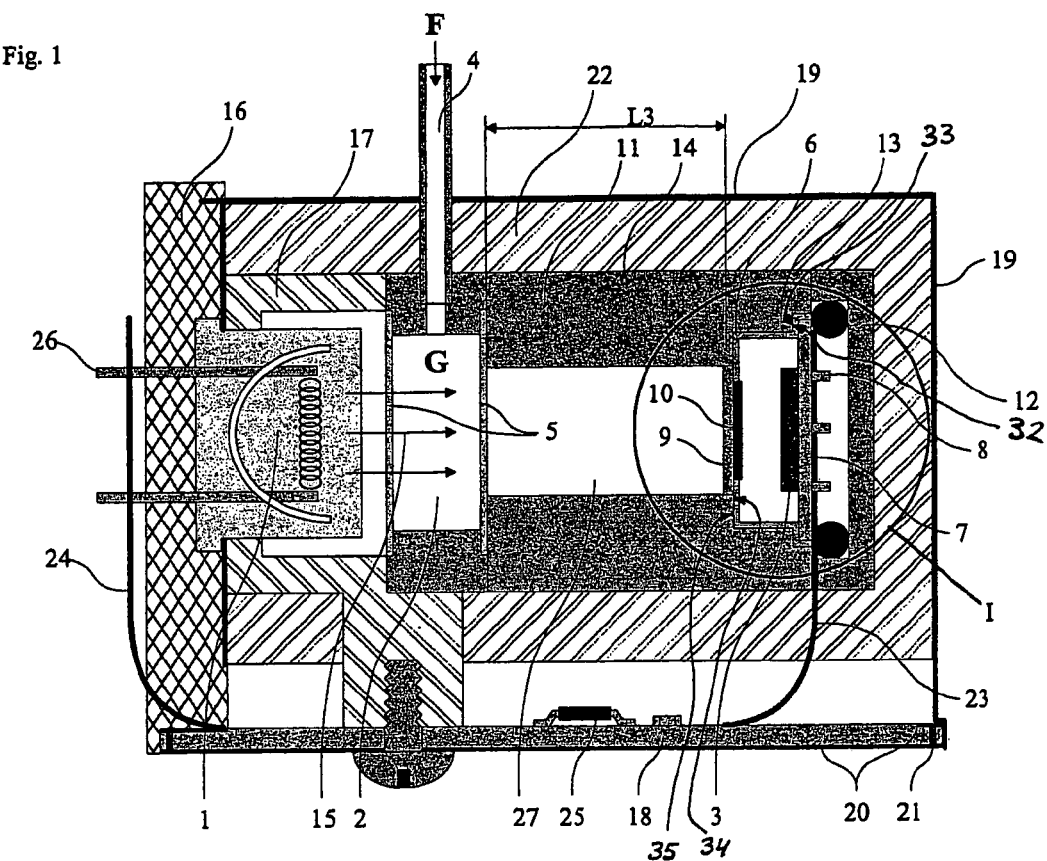
FIG. 1 illustrates the first embodiment of a small gas analyzer according to the invention seen in the longitudinal section of the analyzer parallel with the radiation beam, i.e. along the optical axis. Here the first shield type of the analyzer is especially visualized.

The small sized or miniature gas analyzers for analyzing, e.g. measuring the concentration of one or several gas components are shown in figures. The analyzer comprises a measuring volume 2, made of metal, e.g. aluminum or copper or a plastic or a polymer, between the infrared source 1 and the detector(s) 3. The measuring volume has connections 4 for input and output flow (not shown) of a sample gas mixture G. The measuring volume 2 can be a closed measuring chamber. Alternatively the measuring volume 2 can be a generally open space, i.e. a substantially non-bordered room open to ambience, whereupon the flow F of the gas mixture G into and out of this non-bordered room is caused e.g. by natural movements in the surrounding atmosphere. The measuring volume has first and second ends 5 transparent to radiation. Concerning the embodiment provided with the measuring chamber these transparent ends are typically two windows forming the ends of the volume 2.

The two windows forming said ends 5 are made of a material that transmits the infrared radiation used for the gas measurement. Typical window materials can be sapphire or calcium fluoride. The chamber forming the measuring volume 2 can be made of glass or metal for fast temperature stabilization and increase of thermal mass, but it can also be made of other suitable materials like polymers for better insulation between the source and the detector. The length of the measuring volume 2 depends on the application and concentration range to be measured. For carbon dioxide in the patient breathing gas the length of the volume 2 is normally 3 mm–10 mm.

The detector section of the gas analyzer comprises at least one thermal detector 3 having an active radiation detecting sensor element within at least one detector housing or one support structure 6, when generally defined, and receiving the radiation exiting the measuring volume 2, and the thermal detector has a reference sensor element within the same support structure and protected from said radiation. The thermal detector generates an output signal indicative of a property of said at least one gas component of said mixture in the measuring volume. This property of the at least one gas component is radiation absorption of said gas component over a predetermined wavelength band. The thermal detector, mostly a thermopile, can be purchased as mounted in a standard metal housing 6. There are several different constructions for the thermal detector(s) that can be used in analyzers according to the invention. The typical modern thermopile is manufactured using standard silicon wafer technology with micromachining. The two different thermoelectric materials can be two different metals like bismuth and antimony but they can also be differently doped silicon. The conductors of these two thermoelectrically different materials have typically two sets of junctions, one set of junctions in the center of a membrane with an infrared absorbing layer, called hot junctions, and the other set of junctions above the edge of the silicon substrate, called cold junctions. The substrate chip is mounted with a good thermal contact to the base plate 7 of the support structure 6, which is provided with electrical contact pins 8 for the output of measuring signal(s). The incoming infrared radiation from the source 1 is absorbed at the hot junctions while the cold junctions are supposed to remain at the constant temperature of the base plate. The signal from the thermopile is directly related to the temperature difference between the hot and cold junctions. Thus, with no incoming radiation the temperature difference should ideally be zero and thus the signal should also be zero. However in practice this may not be the case because the cold junctions are at a different temperature than the hot junctions even when the analyzer is in equilibrium because of the temperature difference over the detector section.

The detector section also comprises at least one optical bandpass filter 9 between said active radiation detecting sensor element and said measuring volume 2. The typical support structure(s) or detector housing 6 have a detector window 10 or windows 10 side by side, and the optical bandpass filter can be integrated into the detector housing and would then substitute the window(s). These kinds of detectors are commercially available. Of course one or several separate optical bandpass filter can be arranged in front of the support structure in the radiation beam. For conventional infrared gas measurements with fair selectivity the bandwidth of such a bandpass filter is typically between about 50 nm and 300 nm. A broader bandwidth would only increase the total signal level without increasing the absorption from the gas to be measured. As a consequence, the signal would become very non-linear and larger concentrations would be very difficult to measure with precision, especially if the thermal transients also influence the measurement. A narrower bandwidth can be used if the signal intensity is high enough. In some special cases it may even be advantageous to use a bandwidth of only about 10 nm, but for the radiation absorption of a gas component the predetermined wavelength band has preferably a width of at maximum 400 nm.

Detector section is enclosed in thermal mass 11, 12 formed of a material having high thermal conductance such as metal, e.g. aluminum or copper as the temperature drop across these metal parts is seen to be rather small. The combined thermal mass has a cavity 13 for the housing(s) 6 of the detector(s) 3 and an outer surface 14, whereupon the thermal mass surrounds at least said support structure in the cavity and is in contact with the support structure. The good thermal contact between the combined thermal mass and the support structure ensures fast thermal settling in the gas analyzer and effects upon thermal gradients over the support structure. The thermal mass also extends towards the radiation source 1, at minimum around the second end 5 of the measuring volume 2, which is away from the radiation source and at maximum around the first end 5 of the measuring volume 2, which is nearest to the radiation source, whereupon the second end can be also called as a distal end and the first end as the proximal end of the measuring volume.

A radiation source 1 is arranged in the analyzer to provide a beam 15 of electromagnetic radiation having a wavelength range. Preferably the beam approaches collimation and is directed to pass said measuring volume 2 through the first and second ends 15 thereof. The collimated beam means parallel rays whereas a focused beam means rays radially diverging from or converging to a point or a surface. Deviation should be as small as possible and the rays as parallel as possible. The infrared source 1 is in most cases a broad band emitting hot filament, which has a temperature of at least 300° C. The radiation source can be in the form of a heater wire or small light bulb depending on the required wavelength region. The source can be equipped with concave mirror and or a lens or lenses to collimate the radiation as indicated in the figures. Common to all these radiation sources 1 is that they produce heat. Part of the heat can be dissipated to the surroundings using a suitable heat sink 16 made of metal, e.g. aluminum or copper, which surrounds largely said radiation source, but allows exit of said radiation beam 15. The heat sink can be a separate block of metal, which is in contact with or close to the radiation source like the bulb, or the heat sink can be machined and internally polished to form the concave collimating mirror. The outer surfaces of the heat sink can be designed to comprise e.g. cooling fins for enforced convection, and can be blackened to enforce the radiation of the dead temperature. The cooling can be further enforced by a fan attached to or close to the heat sink, which is not shown in the figures.

Heat will also be conducted along the analyzer body towards the support structure 6 and there will be a temperature gradient between the radiation source and the support structure. In order to adjust the heat flow from the infrared source 1 to the thermal mass and thermal detector the source is thermally insulated. This is done by arranging a thermal barrier 17 between the heat sink 16 and the thermal mass 11, 12. The thermal barrier can be attained by adding an insulating material with low thermal conductivity between the infrared source and the rest of the analyzer, as shown in the figures. The thermal barrier 17 can also be attained by leaving a substantial space between the infrared source and the rest of the analyzer, whereupon the thermal barrier is formed by lack of material. In the particular case shown in figures the thermal barrier is made of solid insulating material with low thermal conductivity to function as a connection point for the electronic circuit board 18 also by offering a firm connection point and an easy way to minimize the conductive thermal flow through the electronic circuit board into the thermal detector.

Figure 2:
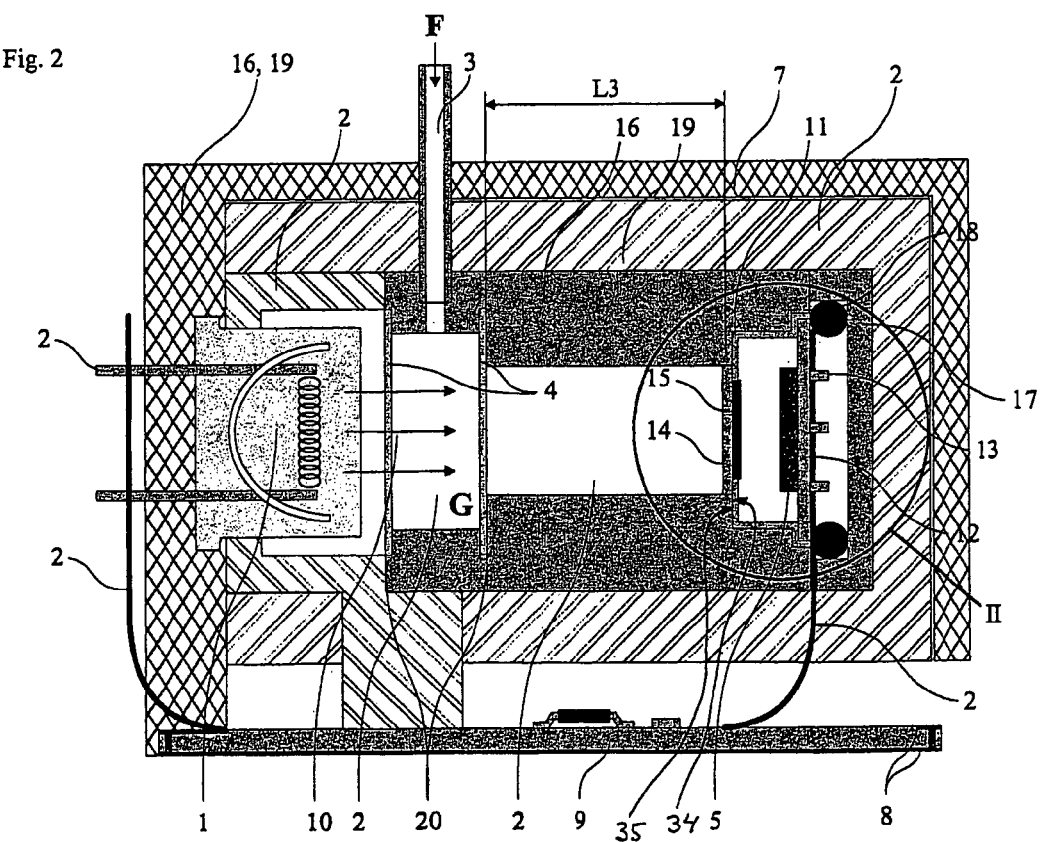
FIG. 2 illustrates the alternative second embodiment of a small gas analyzer according to the invention seen in the longitudinal section of the analyzer parallel with the radiation beam, i.e. along the optical axis. Here the first shield type of the analyzer is especially visualized.
Figure 3A:
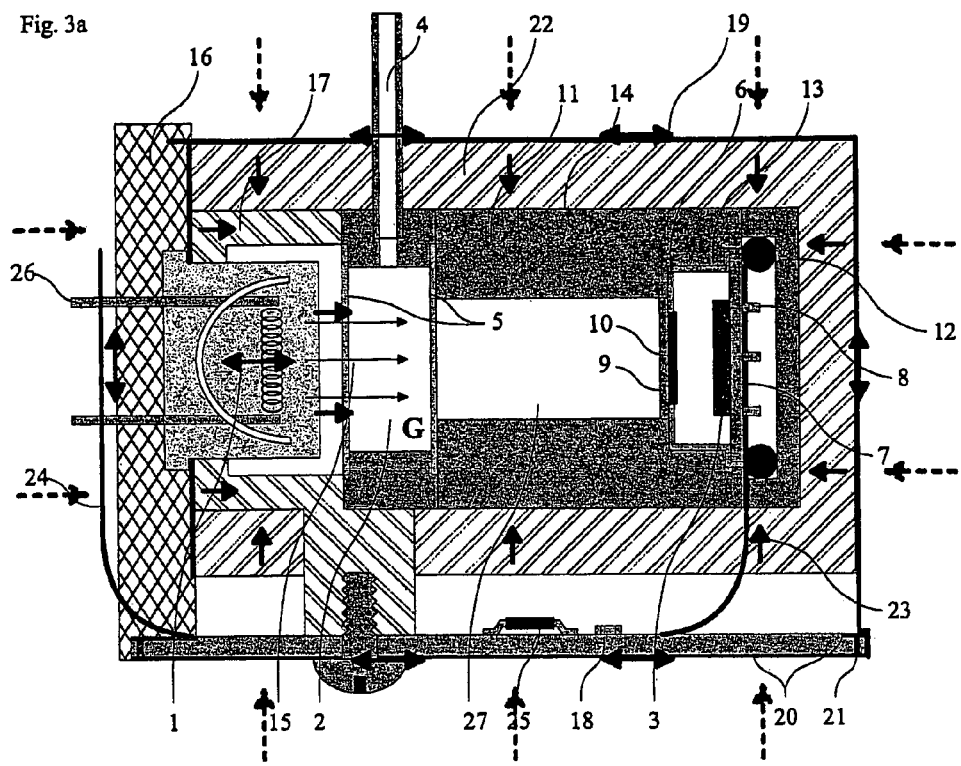
FIG. 3a shows a detailed picture of thermal flows in the analyzer of FIG. 1 construction during the ambient temperature change seen in the longitudinal section of the analyzer parallel with the radiation beam, i.e. along the optical axis.
Figure 3B:
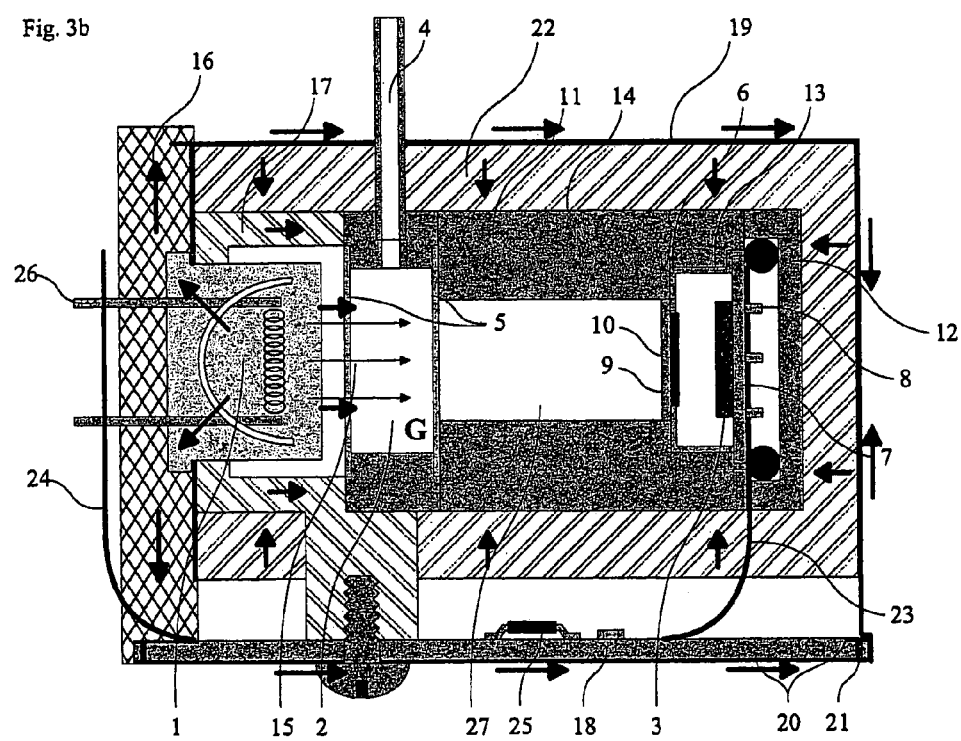
FIG. 3b shows a detailed picture of thermal flows in the analyzer of FIG. 1 construction during the internal temperature transient caused by radiation source at analyzer start-up seen in the longitudinal section of the analyzer parallel with the radiation beam, i.e. along the optical axis.

Dynamic thermal gradients occur mainly as a consequence of changing ambient conditions and changing internal heat flow of the analyzer mainly during the analyzer start-up when the heat starts to flow from the radiation source. These transients or dynamic gradients level out with some time constant but usually last from few minutes to hours. To equalize the dynamic thermal gradients, caused by e.g. ambient changes and analyzer start-up, the thermal mass 11,12 is enclosed in the EMC-shield 19 formed of a material having high thermal and electrical conductance. Thickness of the EMC-housing may vary from few hundredths of millimeters to few millimeters, but preferably it is from 0.1 to 0.5 mm thick. Thinner EMC-housing conducts the temperature rapidly at short distances, but at longer distances temperature difference between the source and the furthest end of the EMC-housing increases because of the temperature losses caused by convection. On the other hand temperature difference between the source and the furthest end of the EMC-housing is smaller in a thicker EMC-housing, but the increase in thermal mass causes slowness to the heat flow around the housing. The EMC-shield can have the shape of a box, as shown in FIGS. 1, 3, 4 and 5, with two sides left open where the heat sink 16 functions as a cover closing the one side and the electronic circuit board 18 closing the other side of the box establishing a continuous housing said EMC-housing around the thermal mass. The electronic circuit board 18 has a continuous ground plane 20 as an outermost surface being directly facing ambient conditions, but preferably it has more ground planes to achieve a good thermal conductance over the complete circuit board. If more ground planes are used they are connected together e.g. through connections 21 near the edges of the electronic circuit board or through a completely metal plated sidewalls of the circuit board (not shown). The innermost surface of the electronic circuit board facing thermal mass and detector(s) has electrical connections 23 for the detector 3, connections 24 for the radiation source 1 and connections for the amplifiers 25 and other monitor electronics. Electrical connections are composed of materials and have dimensions producing an overall thermal conductance substantially lower than that of said electrical contact pins 8 in the support structure e.g. a flexible printed circuit board with a board thickness around 0.2 mm, and the wiring thickness of the electrical wires on the flexible base material around 40 um, whereupon the width of the wiring is between 0.1 mm and 0.3 mm. To attain a good continuous thermal conductance over the complete EMC-housing, as well as electromagnetic compatibility, thermal and electrical connections between the EMC-shield 19, the heat sink 16 and the ground plane(s) 20 of the electronic circuit board 18 must be in good contact to each other. If no attention is paid to EMC (Electro Magnetic Compatibility) requirements the heat sink can extend only partly over the analyzer body as shown in FIG. 2 to obtain similar thermal properties for the analyzer construction as described above.

To dampen and slow down the conductive heat flow of thermal transients from the EMC-housing to the thermal mass, a thermal barrier 22 is arranged between the EMC-housing 16, 18, 19 and the thermal mass 11, 12. The thermal barrier can be attained by adding an insulating material with low thermal conductivity between the EMC-housing and the thermal mass, as shown in the figures. The thermal barrier 22 can also be attained by leaving a substantial space between the EMC-housing and the thermal mass, whereupon the thermal barrier is formed by lack of material.

The invention is based on equalizing and eliminating the effects of temperature transients or in other words dynamic thermal gradients over the thermal detector caused by the internal thermal flow changes inside the analyzer or by the ambient temperature changes over the complete analyzer. This is achieved with a new thermal flow design and mechanical construction described previously. Furthermore according to the invention, offset errors in the thermal detector output caused by the dynamic thermal gradients coming from the different sources, can be compensated by adding a correction signal to the detector output signal, which is relative to measured thermopile temperature. Compensation functions to all temperature transients, especially it minimizes the offset error in the detector output during the transient caused by the internal thermal change, but preferably no compensation is needed for any temperature transients since the analyzer is insensitive to thermal transients due to its thermo-mechanical construction.

According to the invention when the ambient temperature changes the heat flow acts on over the complete analyzer. The ambient temperature change can also be local e.g. affecting on the side of the analyzer as in the case of a cooling fan blowing on the one side of the analyzer. The thermally conductive EMC-housing 16, 18, 19 receives all ambient temperature changes including local thermal changes also, which is shown as dotted arrows in FIG. 3*a*, and balances the heat evenly around the thermal mass 11, 12, shown as double-headed arrows in FIG. 3*a*. The thermal barrier 17, 22 beneath the EMC-housing slows down the thermal flow, coming from the inner surfaces of the EMC-housing, through the thermal barrier into the thermal mass 11, 12, shown as short arrows in FIG. 3*a*. The EMC-thermal barrier and thethermal mass function as a low pass filter that damps the amplitude and decreases the rate of change of the thermal transient. Thermal flow is distributed evenly around the thermal mass and temperature difference between any two points of the thermal mass is zero, thus making the dynamic gradient over the thermal detector zero and signal offset or error at the detector output zero.

Further as the internal temperature of the gas analyzer changes in a consequence of e.g. start-up, the heat starts to flow from the radiation source 1 to each direction, but mainly through the heat sink 16 into the thermally conductive EMC-housing 18, 19. The heat spreads around evenly into the EMC-shield 19 and into the ground plane 20 of circuit board 18 from the heat sink 16, shown as long arrows in FIG. 3*b*. Some of the heat is delivered through convection into the ambient air as the heat flows from the radiation source end to the detector end of the analyzer but in the small sized analyzer as in the invention the temperature difference as well as the temperature gradient between any two points in the EMC-housing remains small. Some of the heat conducts from the radiation source 1 through the thermal barrier 17 into the thermal mass 2, 11, 12, but most of the heat conducts from the inner surfaces of the EMC-shield 19 and ground plane 20 of circuit board 18 through the thermal barrier 22 into the thermal mass 2, 11, 12. The thermal barrier 17, 22 slows down the thermal flow into the thermal mass 2, 11, 12, shown as short arrows in FIG. 3*b*, by damping the amplitude and decreasing the rate of change of the thermal transient. Thermal flow is distributed evenly around the thermal mass and temperature difference between any two points in the thermal mass remains close to zero, thus making the dynamic gradient over the thermal detector zero. Essential in the invention is that the thermal balance or the direction of dynamic gradient over the thermal mass and thus the detector can be adjusted by adjusting the thermal conductance of the thermal barriers 17 and 22. The internal thermal change is thus adjusted to correspond the ambient temperature change in thermal sense.

Figure 4A:
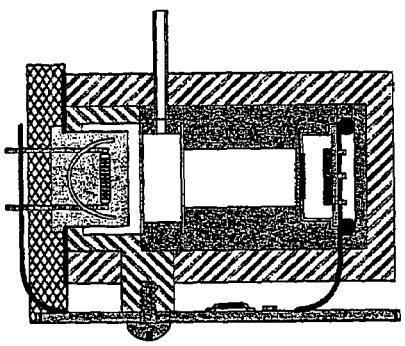
FIGS. 4a–4c illustrates a small gas analyzer according to Prior Art seen in the longitudinal section of the analyzer parallel with the radiation beam, i.e. along the optical axis, and a detailed graph of five different thermal gradients at five different times from start-up of this prior art analyzer, and a graph of thermopile signal during the start-up of this prior art analyzer respectively.
Figure 4B:
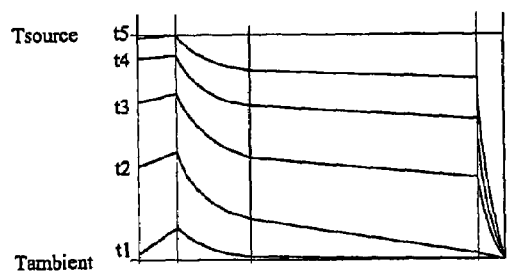
Figure 4C:
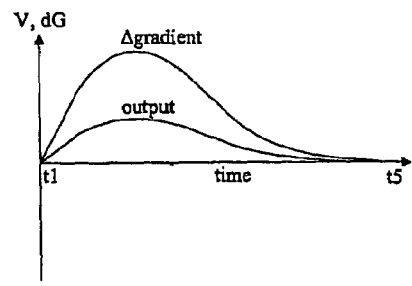

FIG. 4a to 4c shows a prior art embodiment of a small gas analyzer in the longitudinal section of the analyzer parallel with the radiation beam, i.e. along the optical axis. In this construction the heat always flow from the direction of radiation source towards the detector end of the analyzer and there remains a small temperature gradient along the optical axes even in the thermally static state, but in the thermally dynamic state the analyzer will experience a high thermal gradient along its optical axes. The graph of FIG. 4b illustrates dynamic thermal gradients along the optical axes of the analyzer during the thermal transient. The grid in the x-axis illustrates thermal boundaries between different materials along the optical axis and curves in the y-axis illustrate thermal gradients at five different time points, curve t1 right after turning on the radiation source and curve t5 when the analyzer attains the static thermal state. As the radiation source is turned on or as the ambient temperature changes the source starts to warm up faster than its surroundings at t1. Heat starts to flow from the radiation source towards the thermal mass at t2, but the thermal barrier slows down the flow of heat and causes a high temperature difference between the two ends of the thermal mass along the optical axes. At t3 and t4 temperature differences between the two ends of the thermal mass along the optical axes start to even out as the thermal flow rate degreases due to radiation source approaches its thermally static state temperature. At t5 the analyzer has attained its thermally static state and the dynamic thermal gradient becomes zero. The curve output, in the graph of FIG. 4c, illustrates the error in the detector output signal, and the curve Δgradient illustrates the derivative of the dynamic thermal gradient over the thermal detector during the temperature transient.

Figure 5A:
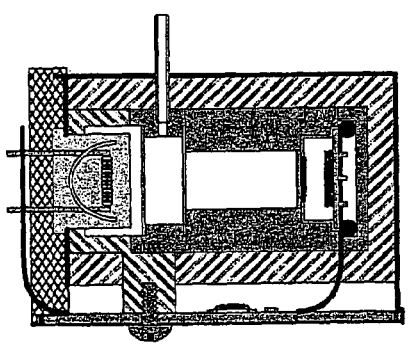
Figure 5B:
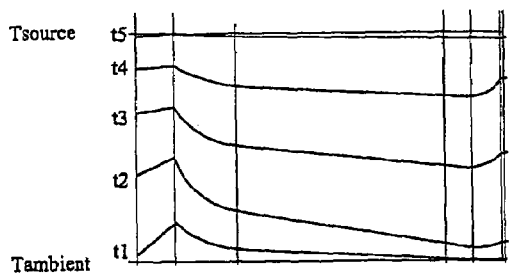
Figure 5C:
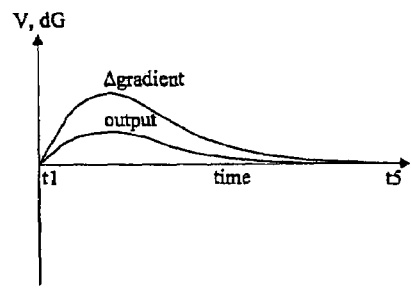
Figure 6A:
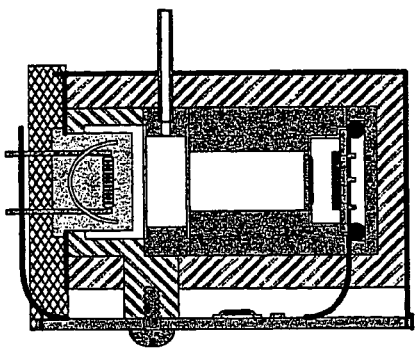
FIGS. 6a–6c illustrates the second embodiment of the inventive gas analyzer seen in the longitudinal section of the analyzer parallel with the radiation beam, i.e. along the optical axis, and a detailed graph of five different thermal gradients at five different times from start-up of this inventive analyzer, and a graph of thermopile signal during the start-up of this inventive analyzer respectively. This embodiment respects to constructions of FIGS. 2 and 8b.
Figure 6B:
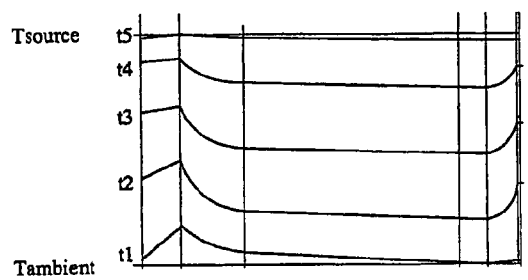
Figure 6C:
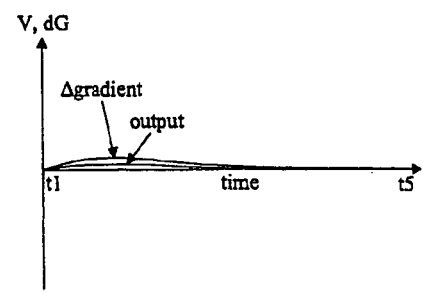
Figure 7A:
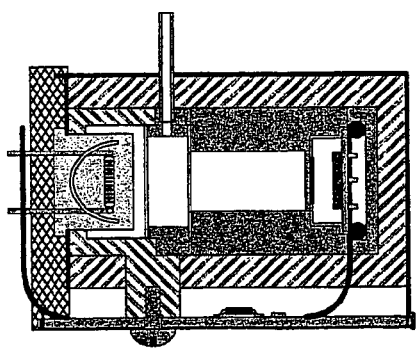
FIGS. 7a–7c illustrates the second embodiment of the inventive gas analyzer seen in the longitudinal section of the analyzer parallel with the radiation beam, i.e. along the optical axis, and a detailed graph of five different thermal gradients at five different times from start-up of this inventive analyzer, and a graph of thermopile signal during the start-up of this inventive analyzer respectively. This embodiment respects to constructions of FIGS. 2 and 8b, but with different dimensions as compared to FIGS. 6a to 6c.
Figure 7B:
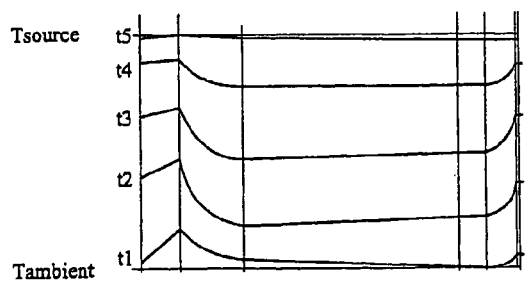
Figure 7C:
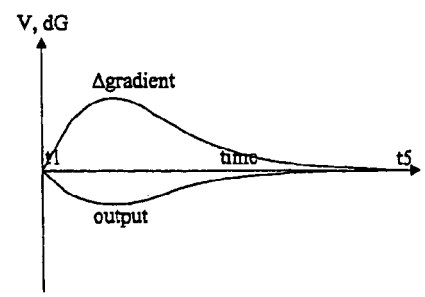

FIGS. 5a to 5c, 6a to 6c and 7a to 7c show three different embodiments of a small gas analyzer according to the invention seen in the longitudinal section of the analyzer parallel with the radiation beam, i.e. along the optical axis. The conductance of the thermal barrier is increased in the analyzer shown in FIGS. 5a to 5c by decreasing its length along the optical axes whereas in FIGS. 7a to 7c the conductance of thermal barrier is degreased by increasing its length along the optical axes compared to the analyzer shown in FIGS. 6a to 6c having optimal thermal conductance of the thermal barrier. As the conductance of the thermal barrier 17 in the analyzer shown in FIGS. 5a to 5c is increased from the analyzer shown in FIGS. 6a to 6c, more heat flows from the direction of radiation source towards the detector end of the analyzer straight through the thermal barrier 17 than conducts through the EMC-housing and thermal barrier 22 in to the thermal mass. During the temperature transient the analyzer experiences higher dynamic thermal gradients along its optical axes compared to the optimal construction shown in FIGS. 6a to 6c, although the thermal gradients are still much smaller than that of the prior art embodiment shown in FIGS. 4a to 4c. As the conductance of thermal barrier 17 in the analyzer shown in FIGS. 7a to 7c is decreased compared to the analyzer shown in FIGS. 6a to 6c, less heat flows straight through the thermal barrier 17 in to the thermal mass than conducts through the EMC-housing and thermal barrier 22 in to the thermal mass. During the temperature transient the analyzer in FIGS. 7a to 7c experiences lower thermal gradients along its optical axes compared to the optimal construction shown in FIGS. 6a to 6c, but compared to the construction shown in FIGS. 5a to 5c the thermal balance becomes opposite. This can be seen by comparing graphs shown in FIGS. 5b, 6b and 7b illustrating the dynamic thermal gradients along the optical axes of the analyzer during the thermal transient and graphs in FIGS. 5c, 6c and 7c illustrating the error signal in the thermopile detector output and the derivative of the dynamic thermal gradient over the thermal detector during the temperature transient similarly as was shown in FIGS. 4a to 4c. As the radiation source is turned on or as the ambient temperature changes the source starts to warm up faster than its surroundings at t1 in FIGS. 5a to 5c, 6a to 6c and 7a to 7c. Heat starts to flow from the radiation source 1 through the thermal barrier 17 and through the EMC-housing and thermal barrier 22 towards the thermal mass 2, 11, 12 at t2. The thermal barrier 17 in FIGS. 5a to 5c slows down the flow of heat less than the optimal thermal barrier 17 shown in FIGS. 6a to 6c causing a temperature difference between the two ends of the thermal mass along the optical axes, whereas the thermal barrier 17 in FIGS. 7a to 7c slows down the flow of heat more than the optimal thermal barrier 17 shown in FIGS. 6a to 6c causing an opposite temperature difference between the two ends of the thermal mass along the optical axes compared to FIGS. 5a to 5c. The opposite temperature differences between the two ends of the thermal mass along the optical axes in FIGS. 5a to 5c and FIGS. 7a to 7c cause different error signals in to the detector outputs shown in FIGS. 5c and 7c since the thermal gradients over the thermopiles are opposite whereas in the optimum construction according to the invention, shown in FIGS. 6a to 6c, the thermal dynamic gradient is zero or close to zero. At t3 and t4 in FIGS. 5a to 5c and FIGS. 7a to 7c temperature differences between the two ends of the thermal mass along the optical axes start to even out, as well as the error signal at the detector output, as the thermal flow rate degreases due to the radiation source approaching its thermally static state temperature. At t5 analyzers in FIGS. 5a to 5c, 6a to 6c and 7a to 7c have attained the thermally static state and thermal dynamic gradient becomes zero as well as the error signal caused by the transient in the detector output since the transient is over.

Theoretically the dark level of the gas analyzer, which means signal from the thermal detector 3 in the absence of any radiation from the radiation source 1, can be considered to be zero during the thermal transient if all thermal gradients within the support structure 6 are eliminated. According to the invention, dynamic thermal gradients during the ambient temperature change or the internal temperature change can be considered to be zero in the construction shown in figures and described previously since the thermal flow is transferred to the thermal mass uniformly from each direction and temperature difference along the thermal mass and thus over the thermal detector is zero. With some thermopile detectors the inner construction of the thermopile can cause temperature gradients inside the detector that cannot be removed by conventional ways. The inner structure of the thermopile detector is such that dynamic gradients are generally present since the set of hot junctions in the center of the membrane are slightly insulated from the base plate of the support structure compared to the set of cold junctions above the edge of the silicon substrate, which in turn is in good thermal contact to the base plate of support structure. In the thermally static state these hot and cold junctions reach the same temperature if the thermal gradients within the support structure have been eliminated, but in the thermal dynamic state the temperature of the slightly insulated hot junctions change with some time delay compared to the temperature of the cold junctions in good thermal contact with the base plate of the support structure. This temperature difference between the cold and the hot junctions can be seen as a dark level or an offset error signal in the detector output which amplitude changes proportionally to the rate of temperature change over the support structure and which approaches zero as the rate of temperature change decreases.

Figure 8A:
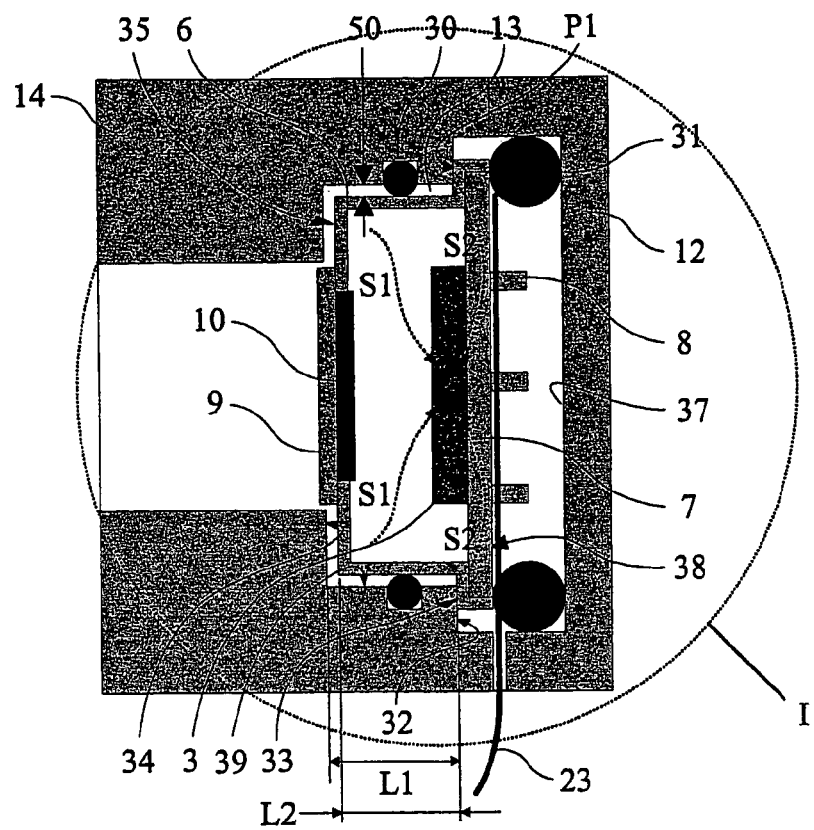
FIGS. 8a and 8b illustrates two different embodiments of thermal connections of the thermal detector mounted in to the thermal mass of a small gas analyzer according to the invention seen in the longitudinal section of the analyzer parallel with the radiation beam, i.e. along the optical axis.

With a thermal and mechanical design, according to the invention, it is possible to degrease or even to eliminate the dynamic gradients caused by the thermal flow differences between the hot and cold junctions inside the thermopile detector. Usually the thermal detector is placed in to the cavity 13 shown in FIG. 8a. The diameter of the cavity 13 must be bigger than the diameter of the support structure 6 due to the tolerances in the diameter of the support structure, whereupon a radial gap 50 between the thermal mass and the support structure exist. The thermal detector 3 centers in to the middle of the cavity 13 by the o-ring 30 placed between the support structure 6 and the channel in the inner wall of the cavity 13, which produces a pressing force directed to the periphery of the support structure 6. Accordingly, there is at least one ring of elastic material between said support structure and an inner wall 39 of said cavity, for centring and maintaining the radial gap 50. Another o-ring 31 presses the thermal detector towards the radiation source 1 so that the circular edge 33 in the support structure 6 is in good thermal contact against the circular step 32 in the cavity 13. Accordingly, there is press means like a washer or ring of elastic material between the back face 38 of said support structure and the bottom wall 37 of the cavity. The thermal connection between the thermal mass 11, 12 and the thermal detector 3 is predominantly through the base plate 7 in the support structure 6 due to space between the support structure 6 and the cavity 13. The cavity of the thermal mass has a bottom step 34 and a rim 32, and a first length L1 therebetween, and the at least one support structure has a frontal edge 35 and a base plate lip 33, and a second length L2 therebetween. When the press means 31 urges the support structure in said cavity a more efficient thermal contact is either between said frontal edge and said bottom step, or between said base plate lip and said rim—as in the embodiment of FIG. 8a—depending on the predetermined difference between said first length L1 and said second length L2. In this case the main thermal contact P1 is between the base plate lip 33 and the rim 32. The thermal flow conducts through the base plate in to the set of cold junctions above the edge of the silicon substrate first and after some delay to the set of hot junctions in the center on the slightly insulated membrane. Theoretically the thermal gradient is thus from the cold junctions to the hot junctions and the amplitude of the offset signal in the output is negative. In this particular case the direction of the dynamic thermal gradient can further be adjusted by filling up the empty space in the cavity 13 around the support structure 6 partly or completely with thermally conductive material, e.g. thermally conductive silicone, to increase the thermal flow through the support structure. As the support structure heats up with its surrounding thermal mass through the thermally conductive material in the cavity 13 part of the heat is transferred through the convection and some through the radiation from the inner walls of the support structure in to the set of hot junctions, which balances the thermal gradient between the hot and cold junctions making it to approach zero. There is also a radiation channel 27 inside the thermal mass, which radiation channel having a third length L3 between said measuring volume and said thermal detector.

Figure 8B:
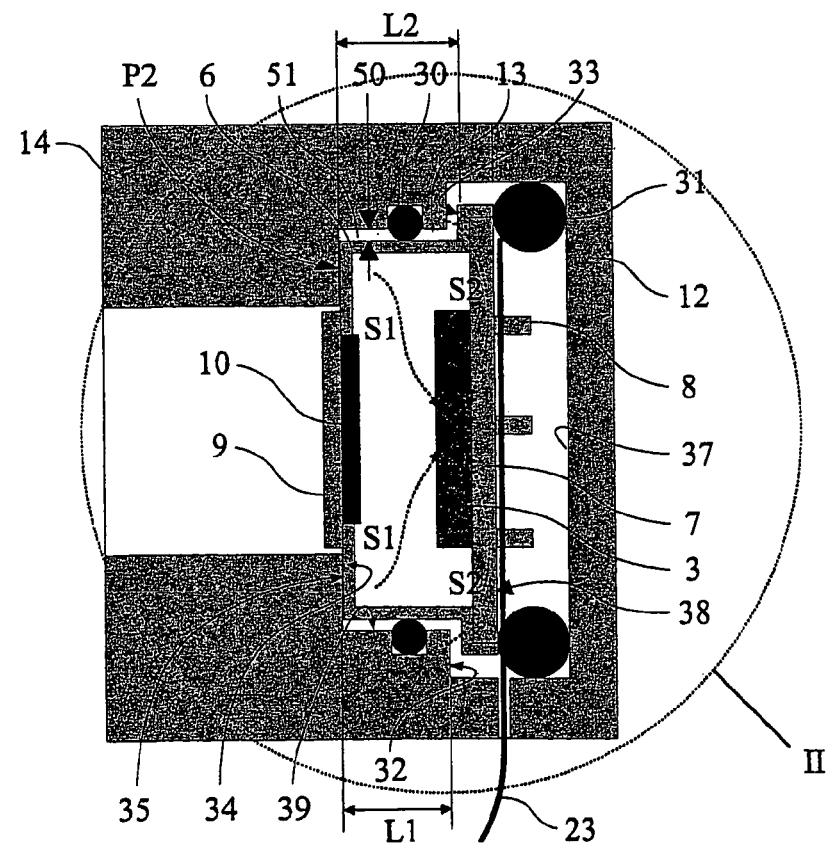

Another more drastic way to influence the thermal gradient between the hot and cold junctions is shown in FIG. 8b. The thermal detector 3 centers in to the middle of the cavity 13 by o-ring 30 placed between the support structure 6 and the channel in the inner wall of cavity 13, which produces a pressing force directed to the periphery of the support structure 6, whereupon a radial gap 50 between the thermal mass and the support structure exist. At least one ring of elastic material is positioned between the support structure and the inner wall 39 of said cavity, for centring the support structure and maintaining the radial gap 50. Another o-ring 31 presses the thermal detector towards the radiation source 1 against the circular step 34 between the radiation channel 27 and the cavity 13 so that the thermal detector 3 is in good thermal contact with the circular step 34 through the window 10 end of the support structure 6. Accordingly, there is press means like a washer or ring of elastic material between the back face 38 of said support structure and the bottom wall 37 of the cavity. The space between the circular edge 33 in the support structure 6 and the circular step 32 of the cavity 13, as well as the space between the support structure 6 and the cavity 13, prevent the thermal flow straight through the base plate 7 in to the thermal detector 3. The cavity of the thermal mass has a bottom step 34 and a rim 32, and a first length L1 therebetween, and the at least one support structure has a frontal edge 35 and a base plate lip 33, and a second length L2 therebetween. When the press means 31 urges the support structure in said cavity a more efficient thermal contact is either between said frontal edge and said bottom step—as in the embodiment of FIG. 8b—or between said base plate lip and said rim depending on the predetermined difference between said first length L1 and said second length L2. In this case the main thermal contact P2 is between the frontal edge 35 and the bottom step 34. The thermal flow now conducts from the window 10 end of the support structure 6 and first associates with the set of hot junctions through convection and radiation and after that with the set of cold junctions above the edge of the silicon substrate through conduction. As the thermal mass on the base plate 7 end is larger compared to the window 10 end of the thermal detector 3 it takes a longer time for the base plate 7 and thus for the cold junctions to attain the same temperature with the window 10 end of the thermal detector 3. Theoretically the dynamic thermal gradient is now from the hot junctions to the cold junctions and the amplitude of the offset signal in the output is positive. In this particular case the direction of the thermal dynamic gradient can further be adjusted by filling up the empty space in the cavity 13 around the support structure 6 partly or completely with thermally conductive material, e.g. thermally conductive silicone, to increase the thermal flow through the support structure 6 and the base plate 7, i.e. a permanently mouldable material 51 between selected areas of said radial gap. As the base plate heats up with its surrounding thermal mass through the thermally conductive material in the space in cavity 13 more heat conducts in to the set of cold junctions balancing the thermal dynamic gradient between the hot and cold junctions and making it to approach zero. In practice different thermal detector designs even from the same manufacturer behave differently in the same analyzer design, which means that the gas analyzer must be designed specifically to use a certain thermal detector.

As summarized, the temperature differences around the thermal detector(s) 3 are evened out by allowing heat to be conducted in a thermal mass 11, 12 having high thermal conductance and dimensions to surround said thermal detector and extending towards the radiation source 1. The thermal mass 11, 12, the measuring volume 3, and the radiation source 1 are thermally isolated from ambience by at least one thermal barrier, either the first thermal barrier 17, or the second thermal barrier 22, or both the first and the second thermal barrier 17 and 22. Heat generated by the radiation source and transferred to the heat sink 16 are conducted along the at least thermally conductive outer surface layers 19, i.e. along the shield. One or several contacts P1 and/or P2 are arranged between support structure 6 of the thermal detector and said thermal mass such that mean heat flow times between the contacts P1, P2 and said reference sensor element along a convection route S1 and a conduction route S2 are at least approaching each other.

Furthermore differences in the conductance of the thermal barrier between the EMC-housing and the thermal mass or between the joints in the thermal mass with poor thermal conductivity can cause dynamic temperature gradients over the thermal mass and the thermal detector. If the error signal in the detector output caused by the thermal dynamic gradient cannot be eliminated with a better thermal design the thermal dynamic gradient appearing during the internal thermal change can still be adjusted to correspond to the dynamic gradient during the ambient temperature change by adjusting the conductance of the thermal barriers and thereby the known temperature compensating methods can be used to minimize the remaining offset error in the detector output signal.

According to the invention the problems in the prior art gas analyzers are solved by equalizing the thermal transients, or dynamic gradients over the complete analyzer and furthermore eliminating thermal transients over the thermal detector, caused by different transient sources e.g. ambient temperature change and analyzer start-up.

The invention is particularly suited to applications in which the infrared radiation intensity within a narrow wavelength region is determined by direct or indirect measurement of the temperature difference produced between the sensor element receiving the impinging radiation and a reference element. Such a detector has the inherent shortcoming that a persisting or changing thermal gradient may disturb the internal balance of the detector, and consequently, the output signal will contain an offset error, which degrades the accuracy of the gas analyzer. The thermal detector used in the measurement may advantageously be a thermopile detector. The method according to the invention s suited for use in gas analyzers designed to perform identification or measurement of the concentration of at least one component of a sample gas mixture.

In the description above some preferred embodiments of an improved non-dispersive infrared gas analyzer have been presented. It will be understood by those skilled in the art that various changes in details may be made without departing from the spirit and scope of the invention as defined by the appended claims.

The invention claimed is:

1. A gas analyzer comprising:
   a measuring volume for through flow of a sample gas mixture, at least one gas component of which is to be analyzed for determining its concentration in said mixture, and having first and second transparent ends;
   a radiation source for providing a beam of electromagnetic radiation having a wavelength range, said beam directed to pass said measuring volume through said first and second transparent ends thereof;
   a heat sink for said radiation source;
   at least one thermal detector having an active radiation detecting sensor element with at least one support structure and receiving the radiation exiting said measuring volume, said thermal detector having a reference sensor element within the same support structure and protected from said radiation, said thermal detector generating an output signal indicative of a property of said at least one gas component of said mixture in the measuring volume;
   a thermal mass: formed of a material having high thermal conductance; having a cavity; being at least in partial thermal contact with said support structure inside said cavity; and extending towards the radiation source;
   a first thermal barrier between the heat sink and the thermal mass;
   a second thermal barrier surrounding the thermal mass and extending towards the heat sink; and
   shield formed of a material or materials having high thermal conductance; said shield being at least in thermal contact with said heat sink, and covering said second thermal barrier.

2. A gas analyzer of claim 1, further comprising:
   in said cavity of the thermal mass a bottom step and a rim, and a first length therebetween;
   in said at least one support structure: a frontal edge and a base plate lip, and a second length therebetween;
   a radial gap between the thermal mass and the support structure; and
   press means urging said support structure in said cavity; whereupon, depending on the predetermined difference between said first length and said second length, a more efficient thermal contact is either between said frontal edge and said bottom step, or between said base plate lip and said rim.

3. A gas analyzer of claim 1, wherein material of said shield is metal plate or plating having thickness of at least 0.03 and at maximum 5 mm.

4. A gas analyzer of claim 3, wherein the metal plate or plating of said shield has a thickness of at least 0.1 and at maximum 0.5 mm.

5. A gas analyzer of claim 1, wherein said shield is a box with one open side to be closed by said heat sink.

6. A gas analyzer of claim 1, wherein said shield is a box with two open sides to be closed by said heat sink and by a printed circuit board respectively.

7. A gas analyzer of claim 6, wherein said printed circuit board comprises a continuous ground layer being at least in thermal contact with said heat sink, and forming a portion of said shield, said ground layer being an outermost surface of the printed circuit board and facing ambience.

8. A gas analyzer of claim 7, said printed circuit board comprising additional ground layers forming portions of said shield.

9. A gas analyzer of claim 1, wherein said shield is a box integral with the heat sink with one open side to be closed by a printed circuit board.

10. A gas analyzer of claim 9, wherein said printed circuit board comprises a continuous ground layer being at least in thermal contact with said heat sink, and forming a portion of said shield, said ground layer being an outermost surface of the printed circuit board and facing ambience.

11. A gas analyzer of claim 1, wherein said first thermal barrier is of a heat insulating material.

12. A gas analyzer of claim 1, wherein said first thermal barrier is a gas or air space.

13. A gas analyzer of claim 1, wherein said second thermal barrier is of a heat insulating material.

14. A gas analyzer of claim 1, wherein said second thermal barrier is a gas or air space.

15. A gas analyzer of claim 11, wherein said heat insulating material is a solid porous material.

16. A gas analyzer of claim 1, wherein said measuring volume is a closed measuring chamber with inlet and outlet tubes, or a generally non-bordered room open to ambience.

17. A gas analyzer of claim 1, wherein said thermal detector is a thermopile.

18. A gas analyzer of claim 1, wherein said property of the at least one gas component is radiation absorption of said gas component over a predetermined wavelength band.

19. A gas analyzer of claim 1, further comprising a radiation channel inside the thermal mass, said radiation channel having a third length between said measuring volume and said thermal detector.

20. A gas analyzer of claim 19, wherein said second thermal barrier surrounding said thermal mass with radiation channel, extends to surround said first thermal barrier and said measuring volume up to the heat sink.

21. A gas analyzer of claim 1, wherein said radiation source is a broadband emitting hot filament having a temperature of at least 300° C.

22. A gas analyzer of claim 1, wherein said material of said thermal mass and said heat sink is a metal or a ceramic.

23. A gas analyzer of claim 2, further comprising a permanently moldable material between selected areas of said radial gap, said permanently moldable material having a high thermal conductance.

24. A gas analyzer of claim 2, further comprising at least one ring of elastic material between said support structure and an inner wall of said cavity, for centering and maintaining said radial gap.

25. A gas analyzer of claim 1, further comprising at least one optical bandpass filter between said active radiation detecting sensor element and said radiation source.

26. A gas analyzer comprising:
a measuring volume for through flow of a sample gas mixture, at least one gas component of which is to be analyzed for determining its concentration in said mixture, and having first and second transparent ends;
a radiation source for providing a beam of electromagnetic radiation having a wavelength range, said beam directed to pass said measuring volume through said first and second transparent ends thereof;
a heat sink for said radiation source;
at least one thermal detector having an active radiation detecting sensor element with at least one support structure and receiving the radiation exiting said measuring volume, said thermal detector having a reference sensor element within the same support structure and protected from said radiation, said thermal detector generating an output signal indicative of a property of said at least one gas component of said mixture in the measuring volume;
a thermal mass: formed of a material having high thermal conductance;
having a cavity with a bottom step and a rim, and a first length therebetween; and
extending towards the radiation source;
in said at least one support structure: a frontal edge and a base plate lip, and a second length therebetween;
a radial gap between the thermal mass and the support structure; and
press means urging said support structure in said cavity; whereupon, depending on the predetermined difference between said first length and said second length, a more efficient thermal contact is either between said frontal edge and said bottom step, or between said base plate lip and said rim.

27. A gas analyzer of claim 26, further comprising:
a first thermal barrier between the heat sink and the thermal mass;
a second thermal barrier surrounding the thermal mass and extending up to the heat sink; and
shield formed of a material or materials having high thermal conductance; said shield being at least in thermal contact with said heat sink, and covering said second thermal barrier.

28. A gas analyzer of claim 26, wherein said first length is larger than said second length, whereupon said thermal contact is between said base plate lip and said rim.

29. A gas analyzer of claim 26, wherein said first length is smaller than said second length, whereupon said thermal contact is between said frontal edge and said bottom step.

30. A gas analyzer of claim 26, further comprising a permanently moldable material between selected areas of said radial gap, said permanently moldable material having a predetermined thermal conductance.

31. A gas analyzer of claim 26, further comprising at least one ring of elastic material between said support structure and an inner wall of said cavity, for centering and maintaining said radial gap.

32. A gas analyzer of claim 31, wherein said at least one ring borders preselected areas of said radial gap filled with a permanently moldable material having a high thermal conductance.

33. A gas analyzer of claim 30, wherein said permanently moldable material is a silicone polymer based grease or jelly.

34. A gas analyzer of claim 26, wherein said press means are a washer or ring of elastic material between a back face of said support structure and a bottom wall of said cavity.

35. A gas analyzer of claim 27, wherein said first thermal barrier and/or said second thermal barrier is a gas or air space.

36. A gas analyzer of claim 27, wherein said first thermal barrier and/or said second thermal barrier comprises a heat insulating material in a form of a solid porous material.

37. A gas analyzer of claim 26, wherein said measuring volume is a closed measuring chamber with inlet and outlet tubes, or a generally non-bordered room open to ambience.

38. A gas analyzer of claim 26, wherein said thermal detector is a thermopile.

39. A gas analyzer of claim 26, wherein said property of the at least one gas component is radiation absorption of said gas component over a predetermined wavelength band.

40. A gas analyzer of claim 26, further comprising a radiation channel inside the thermal mass, said radiation channel having a third length between said measuring volume and said thermal detector.

41. A gas analyzer of claim 27, wherein said second thermal barrier surrounding said thermal mass with a radiation channel, extends to surround said first thermal barrier and said measuring volume up to the heat sink.

42. A gas analyzer of claim 26, wherein said radiation source is a broadband emitting hot filament having a temperature of at least 300° C.

43. A gas analyzer of claim 26, wherein said material of said thermal mass and said heat sink is a metal or a ceramic.

44. A gas analyzer of claim 27, wherein material of said shield is metal plate or plating having thickness of at least 0.03 and at maximum 5 mm.

45. A gas analyzer of claim 27, wherein said shield is a box with one or two open sides to be closed by said heat sink and/or by a printed circuit board.

46. A gas analyzer of claim 45, wherein said printed circuit board comprises a continuous ground layer being at least in thermal contact with said heat sink, and forming a portion of said shield, said ground layer being an outermost surface of the printed circuit board and facing ambience.

47. A gas analyzer of claim 26, further comprising at least one optical bandpass filter between said active radiation detecting sensor element and said radiation source.

48. A method for determining a concentration of at least one gas component in a sample gas mixture by providing a radiation source that directs a beam of electromagnetic radiation having a wavelength range to pass a measuring volume, through which said sample gas mixture is delivered, and by detecting intensity of a rest radiation exiting said measuring volume and said at least one optical bandpass filter, the method comprising the steps of:

transferring generated heat from said radiation source to a heat sink;

allowing said rest radiation to hit an active radiation detecting sensor element in a thermal detector and protecting a reference sensor element of the same thermal detector from said rest radiation; said thermal detector having a support structure carrying said detecting and reference sensor elements, and generating an output signal indicative of a property of said at least one gas component of said mixture in the measuring volume;

evening out temperature differences around said thermal detector by allowing heat to be conducted in a thermal mass having high thermal conductance and dimensions to surround said thermal detector and extending towards said radiation source;

thermally isolating said thermal mass, said measuring volume, and said radiation source from ambience by at least one thermal barrier;

conducting said generated heat from said heat sink along at least thermally conductive outer surface layers;

arranging one or several contacts between said support structure of the thermal detector and said thermal mass such that mean heat flow times between said one or several contacts and said reference sensor element along a convection route and a conduction route are at least approaching each other.

49. A gas analyzer of claim 13, wherein said heat insulating material is a solid porous material.

50. A gas analyzer of claim 32, wherein said permanently moldable material is a silicone polymer based grease or jelly.

* * * * *